US010016480B2

(12) United States Patent
Rudloff et al.

(10) Patent No.: US 10,016,480 B2
(45) Date of Patent: Jul. 10, 2018

(54) PEPTIDE-BASED METHODS FOR TREATING PANCREATIC CANCER

(71) Applicants: The United States of America, as represented by the Secretary, Department of Health and Human Services, Washington, DC (US); Riptide Bioscience, Inc., Vallejo, CA (US)

(72) Inventors: Udo Rudloff, Bethesda, MD (US); Jesse M. Jaynes, Auburn, AL (US); Henry W. Lopez, Napa, CA (US); George R. Martin, Rockville, MD (US); Clayton Yates, Auburn, AL (US)

(73) Assignees: The United States of America, as Represented by the Secretary, Dept. of Health and Human Services, Washington, DC (US); Riptide Bioscience, Inc., Vallejo, CA (US)

( * ) Notice: Subject to any disclaimer, the term of this patent is extended or adjusted under 35 U.S.C. 154(b) by 0 days.

(21) Appl. No.: 15/518,216

(22) PCT Filed: Oct. 13, 2015

(86) PCT No.: PCT/US2015/055305
§ 371 (c)(1),
(2) Date: Apr. 10, 2017

(87) PCT Pub. No.: WO2016/061087
PCT Pub. Date: Apr. 21, 2016

(65) Prior Publication Data
US 2017/0252396 A1    Sep. 7, 2017

Related U.S. Application Data

(60) Provisional application No. 62/063,909, filed on Oct. 14, 2014.

(51) Int. Cl.

| A61K 38/08 | (2006.01) |
|---|---|
| A61K 45/06 | (2006.01) |
| C07K 7/06 | (2006.01) |
| C07K 7/00 | (2006.01) |
| A61K 47/48 | (2006.01) |
| A61K 31/7068 | (2006.01) |
| A61K 31/337 | (2006.01) |
| A61K 31/513 | (2006.01) |
| A61K 31/519 | (2006.01) |
| A61K 31/4745 | (2006.01) |
| A61K 31/282 | (2006.01) |

(52) U.S. Cl.
CPC ............ *A61K 38/08* (2013.01); *A61K 31/282* (2013.01); *A61K 31/337* (2013.01); *A61K 31/4745* (2013.01); *A61K 31/513* (2013.01); *A61K 31/519* (2013.01); *A61K 31/7068* (2013.01); *A61K 45/06* (2013.01); *A61K 47/48215* (2013.01); *A61K 47/48284* (2013.01)

(58) Field of Classification Search
CPC ............... A61K 31/282; A61K 31/337; A61K 31/4745; A61K 31/513; A61K 31/519; A61K 31/7068; A61K 38/08; A61K 45/06; A61K 47/48215; A61K 47/48284; C07K 7/06; C07K 7/00
USPC ............... 530/300, 328; 514/19.2, 19.3, 21.6
See application file for complete search history.

(56) References Cited

U.S. PATENT DOCUMENTS

| 5,717,064 | A | 2/1998 | Julian et al. |
|---|---|---|---|
| 5,861,478 | A | 1/1999 | Jaynes |
| 5,955,573 | A | 9/1999 | Garbarino et al. |
| 5,962,410 | A | 10/1999 | Jaynes et al. |
| 6,255,282 | B1 | 7/2001 | Jaynes |
| 6,514,692 | B2 | 2/2003 | Jaynes |
| 6,559,281 | B1 | 5/2003 | Jaynes |
| 6,635,740 | B1 | 10/2003 | Enright et al. |
| 7,288,622 | B1 | 10/2007 | Jaynes et al. |
| 7,566,777 | B2 | 7/2009 | Enright et al. |
| 7,803,755 | B2 | 9/2010 | Jaynes |
| 8,734,775 | B2 | 5/2014 | Yates-Binder et al. |
| 2004/0018967 | A1 | 1/2004 | Enright et al. |
| 2005/0187151 | A1 | 8/2005 | Strom et al. |
| 2010/0016227 | A1 | 1/2010 | Enright et al. |
| 2012/0270770 | A1* | 10/2012 | Jaynes ............. C07K 14/43572 514/1.9 |

(Continued)

FOREIGN PATENT DOCUMENTS

| WO | WO9012866 A1 | 11/1990 |
|---|---|---|
| WO | WO9842634 A1 | 10/1998 |
| WO | WO2005046714 A2 | 5/2005 |

OTHER PUBLICATIONS

Ko, Folfirinox: a small step or a great leap forward?, J Clin Oncol. Oct. 1, 2011;29(28):3727-9.
Jaynes et al., Structure/Function Link Between Cytokine Domains and Natural and Designed Lytic Peptides: Medical Promise, 2012 American Chemical Society, pp. 21-45.
Park et al., Melittin Inhibits Inflammatory Target Gene Expression and Mediator Generation Via Interaction With IkappaB Kinase, Biochem Pharmacol. Jan. 15, 2007;73(2):237-47.

(Continued)

*Primary Examiner* — Julie Ha
(74) *Attorney, Agent, or Firm* — Glenn J. Foulds; Bozicevic, Field & Francis LLP

(57) ABSTRACT

Methods for treating a subject for pancreatic cancer via administration of small anti-inflammatory peptides are disclosed. The peptides may be administered in conjunction with another therapeutic agent, such as a chemotherapeutic agent, or therapeutic regimen. In some cases, the anti-inflammatory peptide that finds use in the subject methods has the amino acid sequence Lys-Phe-Arg-Lys-Ala-Phe-Lys-Arg-Phe-Phe (SEQ ID NO:1) or a multimer, derivative, or variant thereof.

17 Claims, 9 Drawing Sheets

(56) References Cited

U.S. PATENT DOCUMENTS

2014/0329753 A1  11/2014  Jaynes

OTHER PUBLICATIONS

Wang et al., A Cell-Penetrating Peptide Suppresses Inflammation by Inhbiting NF-kappa-Beta Signaling, Molecular Therapy, May 10, 2011, vol. 19, No. 10; pp. 1849-1857.
Oxytocin, NCBI, PRF:229114, GI:229114 (Jul. 10, 1992), 1 page.
Jankowski, Anti-inflammatory effect of oxytocin in rat myocardial infarction, Basic Res Cardiol. Mar. 2010;105 (2)205-18.

* cited by examiner

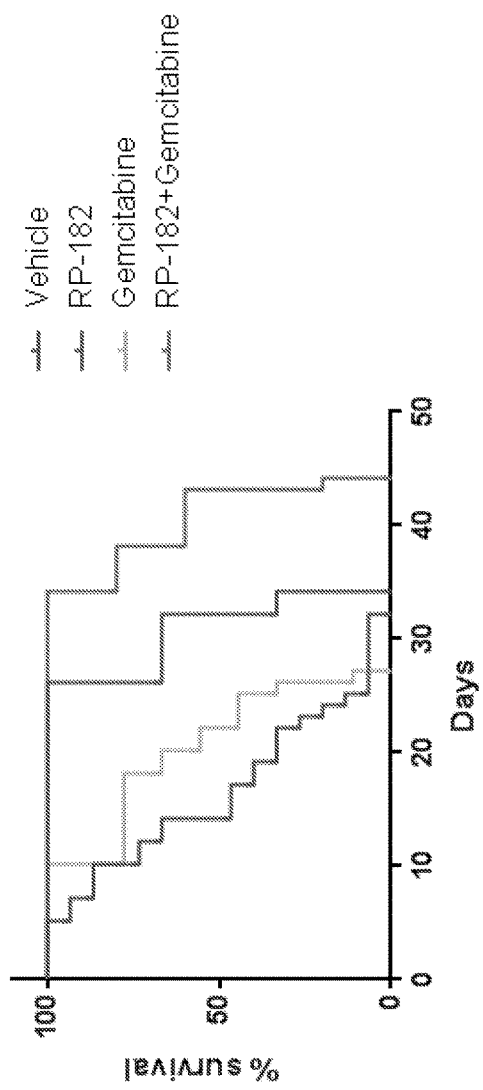

```
                       SEQUENCE LISTING

<160> NUMBER OF SEQ ID NOS: 2

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 1

Lys Phe Arg Lys Ala Phe Lys Arg Phe Phe
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 2

Phe Ala Lys Lys Phe Ala Lys Lys Phe Lys
1               5                   10
```

PEPTIDE-BASED METHODS FOR TREATING PANCREATIC CANCER

RELATED APPLICATION DATA

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

SEQUENCE LISTING DATA

The Sequence Listing text file attached hereto, created Oct. 13, 2015, size 2 kilobytes, filename "6137NCI-38-PCT Sequence listing ST25" is incorporated herein by reference in its entirety.

BACKGROUND

Pancreatic cancer is a disease in which malignant (cancerous) cells form in the tissues of the pancreas. Pancreatic cancer often has a poor prognosis, even when diagnosed early. Pancreatic cancer typically spreads rapidly and is seldom detected in its early stages, which is a major reason why it's a leading cause of cancer death. Indeed, pancreatic cancer is the fourth leading cause of cancer death in both men and women in the United States of America (U.S.), with more than 38,000 deaths annually. Pancreatic cancer is expected to rank second in all cancer-related deaths in the United States by 2020. Furthermore, the 5-year survival rate of pancreas cancer in the U.S. ranks lowest among solid organ tumors. There is no reliable screening test for the early detection of pancreatic cancer. Signs and symptoms may not appear until pancreatic cancer is quite advanced, and complete surgical removal isn't possible.

Standard treatment of pancreatic cancer, including surgery, radiation therapy, and chemotherapy largely show limited efficacy. Indeed, approved treatments including gemcitabine, folfirinox, the combination of gemcitabine and abraxane, and the combination of gemcitabine and erlotinib, improve survival by a few to several months, at best. Newer therapies have not demonstrated much more success, possibly due to the thick stroma and the relative absence of abundant vessels in the pancreas.

SUMMARY

Peptide A, having the amino acid sequence Lys-Phe-Arg-Lys-Ala-Phe-Lys-Arg-Phe-Phe (SEQ ID NO:1), and Peptide B, having the amino acid sequence Phe-Ala-Lys-Lys-Phe-Ala-Lys-Lys-Phe-Lys (SEQ ID NO:2), were evaluated in a number of inflammatory disease models and showed strong activity in all of them.

Pancreatic cancer is unique in that it has a very strong inflammatory component (Farrow, et al. 2004 *Annals of Surgery* 239(6):763-771; Zambirinis, et al. 2015 *Cancer J* 20(3):195-202). It is also unique in its drug diffusion/perfusion requirements—pancreatic tumors do not take up drugs easily (Whatcott, et al. Ch 8: Desmoplasia and chemoresistance in pancreatic cancer 2012 Pancreatic Cancer and Tumor Microenvironment, editors Grippo and Munshi). Additionally, it has been shown that targeting the stroma through the development of stromal therapies can yield effective tumor responses in preclinical models of pancreatic cancer (Olive, et al. 2009 *Science* 324(5933): 1457-61; Provanzano, et al. 2012 *Cancer Cell* 21(3):418-29).

Upon testing peptide A and peptide B in a variety of pancreatic cancer animal models, strong anti-cancer activity of the peptide has been found against pancreas cancer, as described herein. Also described herein is the administration of peptide A or peptide B, in combination with the approved chemotherapy agent gemcitabine, which shrank tumors and extended life of transgenic animals that develop pancreas cancer. Therefore, this disclosure is based on the discovery of peptides that have powerful anti-inflammatory activities in vitro and in vivo, and in another aspect, on the discovery that the peptides are sufficiently stable in the circulation, as also shown by mass spectroscopic measurement allowing determination of their pharmacokinetic and dose-response properties.

This disclosure provides a method of treating pancreatic cancer in a subject, the method comprising administering a pharmaceutical composition comprising the anti-inflammatory peptide A or peptide B, or a variant thereof to the subject.

In another aspect, the invention provides a method of treating pancreatic cancer in a subject, the method comprising administering a pharmaceutical composition comprising the anti-inflammatory peptide A or peptide B, or variants thereof, and at least one chemotherapeutic agent to the subject. These methods may include treating pancreatic cancer in a subject by administering to the subject a peptide comprising the amino acid sequence Lys-Phe-Arg-Lys-Ala-Phe-Lys-Arg-Phe-Phe (SEQ ID NO:1), or Phe-Ala-Lys-Lys-Phe-Ala-Lys-Lys-Phe-Lys (SEQ ID NO:2), or a multimer, derivative, or variant thereof. These methods may include the administration of an additional therapeutic agent. The additional therapeutic agent(s) may be one or more chemotherapeutic agents. Such chemotherapeutic agents may be selected from the group consisting of gemcitabine or an immune checkpoint inhibitor. The chemotherapeutic agent may be gemcitabine Abraxane or the FOLFIRINOX regimen (fluorouracil, leucovorin, irinotecan, oxaliplatin) (J. Clin. Onc. Oct. 1, 2011, 29(28):3727-3729).

In these methods, the administration may be by parenteral administration. In these methods, the peptide may be administered at a dosage of about 0.05 to about 25 mg/kg. In these methods, the subject may be a human.

One aspect is a pharmaceutical composition comprising a peptide comprising the amino acid sequence Lys-Phe-Arg-Lys-Ala-Phe-Lys-Arg-Phe-Phe (SEQ ID NO:1) or Phe-Ala-Lys-Lys-Phe-Ala-Lys-Lys-Phe-Lys (SEQ ID NO:2) or a multimer, derivative, or variant thereof, and a pharmaceutically acceptable carrier for the treatment of pancreatic cancer. These compositions may include at least one additional therapeutic agent, and therefore another aspect is a pharmaceutical composition comprising a peptide comprising the amino acid sequence Lys-Phe-Arg-Lys-Ala-Phe-Lys-Arg-Phe-Phe (SEQ ID NO:1) or Phe-Ala-Lys-Lys-Phe-Ala-Lys-Lys-Phe-Lys (SEQ ID NO:2) or a multimer, derivative, or variant thereof, at least one additional therapeutic agent, and a pharmaceutically acceptable carrier for the treatment of pancreatic cancer. A related aspect is the use of a peptide comprising the amino acid sequence Lys-Phe-Arg-Lys-Ala-Phe-Lys-Arg-Phe-Phe (SEQ ID NO:1) or Phe-Ala-Lys-Lys-Phe-Ala-Lys-Lys-Phe-Lys (SEQ ID NO:2) or a multimer, derivative, or variant thereof for the treatment of pancreatic cancer.

Other aspects of the invention are described in or are obvious from the following disclosure and are within the ambit of the invention.

BRIEF DESCRIPTION OF THE DRAWINGS

The following Detailed Description, given by way of Examples, but not intended to limit the invention to specific embodiments described, may be understood in conjunction with the accompanying figures, in which:

FIG. 1B shows the survival of the transgenic animals treated with the three drug, and control, regimens. The survival curves show that RP-182 significantly improves survival in combination with gemcitabine

DETAILED DESCRIPTION

Figure 1A:
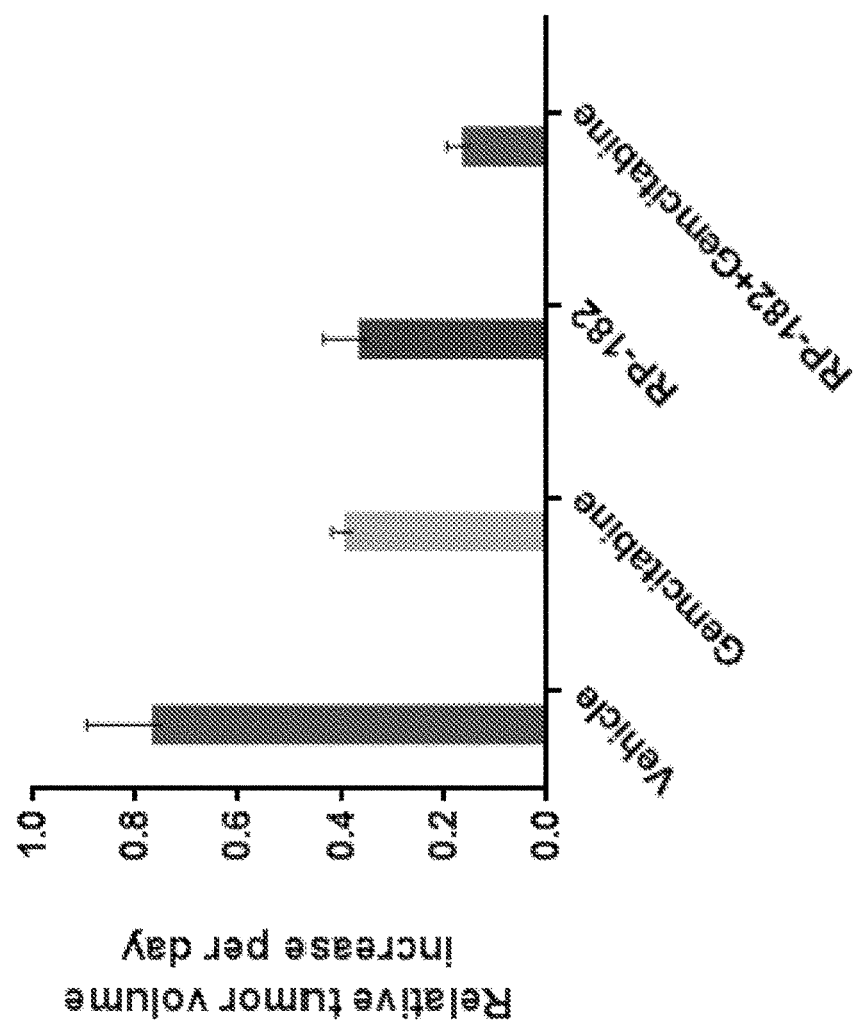
FIG. 1A shows the relative increase in tumor volume in mice with tumors that were randomly assigned to treatment with vehicle ($H_2O$ or PBS); 50 mg/kg gemcitabine; 20 mg/kg Peptide A; or the combination of Peptide A (20 mg/kg) and gemcitabine (50 mg/kg). All treatments were administered by intraperitoneal injection. The results show Peptide A alone halted growth of pancreatic cancers in the transgenic animals and the combination of Peptide A with gemcitabine RP-182 significantly reduces growth of pancreatic cancers in transgenic animals.

As discussed above, the invention disclosed herein relates to the use of anti-inflammatory peptides, particularly peptides having immunosuppressive properties, and methods of administering such peptides to a subject suffering from pancreatic cancer or at risk of developing pancreatic cancer.

Definitions

As used herein, the singular forms "a", "and", and "the" include plural referents, unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

The terms "peptide" and "polypeptide" are used synonymously herein to refer to polymers constructed from amino acid residues.

The term "striapathic region," as used herein, refers to an alternating sequence of hydrophobic and hydrophilic modules. A "hydrophobic module" is made up of a peptide sequence consisting of one to five hydrophobic amino acid residues. Likewise, a hydrophilic module is made up of a peptide sequence consisting of one to five hydrophilic amino acid residues.

"Substantially pure", as used herein, for example, in the context of a pharmaceutical composition, means that the peptide makes up greater than about 50% of the total content of the composition (e.g., total protein of the composition), or greater than about 80% of the total protein content. For example, a "substantially pure" peptide refers to compositions in which at least 80%, at least 85%, at least 90% or more of the total composition is the peptide (e.g. 95%, 98%, 99%, greater than 99% of the total protein). The peptide can make up greater than about 90%, greater than about 95%, greater than 98%, or greater than 99%, of the total protein in the composition. In some embodiments, a peptide is substantially pure when the peptide is at least 60% or at least 75% by weight free from organic molecules with which it is associated during production. In some embodiments, the peptide is at least 60%, at least 75%, at least 80%, at least 85%, at least 90%, at least 95%, or at least 99%, by weight, pure. For example, in some embodiments, an immunomodulatory peptide is substantially pure when the immunomodulatory peptide is at least 60% or at least 75% by weight free from organic molecules with which the peptide(s) is associated during production, in some embodiments, the immunomodulatory peptide is at least 60%, at least 75%, at least 80%, at least 85%, at least 90%, at least 95%, or at least 99%, by weight, pure.

The terms "subject", "patient", and "individual", as used herein interchangeably, refer to a multicellular animal (including mammals (e.g., humans, non-Human primates, murines, ovines, bovines, ruminants, lagomorphs, porcines, caprines, equines, canines, felines, ayes, etc.), avians (e.g., chicken), amphibians (e.g. Xenopus), reptiles, and insects (e.g. Drosophila). "Animal" includes guinea pig, hamster, ferret, chinchilla, mouse, and cotton rat.

"Tumor", as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The term "anti-inflammatory property," as used herein, refers to any property of a polypeptide that can be evaluated, and/or, that reduces or inhibits, or would be expected to reduce or inhibit, a pro-inflammatory signal mediated by a protein target and/or reduces or inhibits inflammation in a subject.

An "effective amount" refers to an amount effective, at dosages and for periods of time necessary, to achieve the desired therapeutic or prophylactic result. A "therapeutically effective amount" of a peptide or pharmaceutical composition comprising a peptide described herein may vary according to factors such as the disease state, age, sex, and weight of the individual, and the ability of the peptide or composition to elicit a desired response in the individual. A therapeutically effective amount is also one in which any toxic or detrimental effects of the peptide or composition comprising the peptide are outweighed by the therapeutically beneficial effects.

Reference herein to any numerical range (for example, a dosage range) expressly includes each numerical value (including fractional numbers and whole numbers) encompassed by that range. For example, but without limitation, reference herein to a range of 0.5 mg/kg to 100 mg/kg explicitly includes all whole numbers of and fractional numbers between the two.

An individual referred to as "suffering from" pancreatic cancer, as described herein, has been diagnosed with and/or displays one or more symptoms of pancreatic cancer.

As used herein, the term "at risk" for pancreatic cancer, refers to a subject (e.g., a human) that is predisposed to developing pancreatic cancer and/or expressing one or more symptoms of the disease. This predisposition may be genetic or due to other factors. It is not intended that the present invention be limited to any particular signs or symptoms. Thus, it is intended that the present invention encompasses subjects that are experiencing any range of pancreatic cancer, from sub-clinical to full-blown, wherein the subject exhibits at least one of the indicia (e.g., signs and symptoms) associated with pancreatic cancer.

The terms "treat," "treatment," or "treating", as used herein, refer to any method used to partially or completely alleviate, ameliorate, relieve, inhibit, prevent, delay onset of, reduce severity of and/or reduce incidence of one or more symptoms or features of a disease, disorder, and/or condition (e.g., pancreatic cancer). Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The terms "comprises", "comprising", are intended to have the broad meaning ascribed to them in US Patent Law and can mean "includes", "including" and the like.

The invention can be understood more fully by reference to the following detailed description and illustrative examples, which are intended to exemplify non-limiting embodiments of the invention.

Polypeptides

Peptide A comprises, consists essentially of, or consists of a peptide having the sequence Lys-Phe-Arg-Lys-Ala-Phe-Lys-Arg-Phe-Phe (SEQ ID NO: 1).

Peptide B comprises, consists essentially of, or consists of a peptide having the sequence Phe-Ala-Lys-Lys-Phe-Ala-Lys-Lys-Phe-Lys (SEQ ID NO:2).

Peptides A and B are stable in serum and can be detected and measured by, for example, (ion trap) mass spectroscopy.

Variant Polypeptides

A "variant" of a peptide described herein is a polypeptide that is substantially similar to a polypeptide disclosed herein and retains at least one anti-inflammatory property or anti-cancer of the subject polypeptide. Variants can include deletions (i.e., truncations) of one or more amino acid residues at the N-terminus or the C-terminus of a subject polypeptide disclosed herein; deletion and/or addition of one or more amino acid residues at one or more internal sites in the subject polypeptide disclosed herein; and/or substitution of one or more amino acid residues at one or more positions in the subject polypeptide disclosed herein. For subject polypeptides that are 12 amino acid residues in length or shorter, variant polypeptides preferably include three or fewer (e.g., two, one, or none) deleted amino acid residues, whether located internally, at the N-terminal end, and/or at the C-terminal end.

Accordingly, the inventive methods and compositions are likewise contemplated for anti-inflammatory polypeptides that are at least 50% identical (e.g., at least 60%, 70%, 80%, 90%, or more) to the anti-inflammatory polypeptides disclosed herein and that retain at least one anti-inflammatory property.

Substituted amino acid residues can be unrelated to the amino acid residue being replaced (e.g., unrelated in terms or hydrophobicity/hydrophilicity, size, charge, polarity, etc.), or the substituted amino acid residues can constitute similar, conservative, or highly conservative amino acid substitutions. As used herein, "similar," "conservative," and "highly conservative" amino acid substitutions are defined as shown in the table, below. The determination of whether an amino acid residue substitution is similar, conservative, or highly conservative is based exclusively on the side chain of the amino acid residue and not the peptide backbone, which may be modified to increase peptide stability, as discussed below.

| Amino Acid | Similar Amino Acid | Conservative Amino Acid Substitutions | Highly Conservative Amino Acid |
| --- | --- | --- | --- |
| Glycine (G) | A, S, N | A | n/a |
| Alanine (A) | S, G, T, V, C, P, Q | S, G, T | S |
| Serine (S) | T, A, N, G, Q | T, A, N | T, A |
| Threonine (T) | S, A, V, N, M | S, A, V, N | S |
| Cysteine (C) | A, S, T, V, I | A | n/a |
| Proline (P) | A, S, T | A | n/a |
| Methionine (M) | L, I, V, F | L, I, V | L, I |
| Valine (V) | I, L, M, T, A | I, L, M | I |
| Leucine (L) | M, I, V, F, T, A | M, I, V, F | M, I |
| Isoleucine (I) | V, L, M, F, T, C | V, L, M, F | V, L, M |
| Phenylalanine (F) | W, L, M, I, V | W, L | n/a |

-continued

| Amino Acid | Similar Amino Acid | Conservative Amino Acid Substitutions | Highly Conservative Amino Acid |
|---|---|---|---|
| Tyrosine (Y) | F, W, H, L, I | F, W | F |
| Tryptophan (W) | F, L, V | F | n/a |
| Asparagine (N) | Q | Q | Q |
| Glutamine (Q) | N | N | N |
| Aspartic Acid (D) | E | E | E |
| Glutamic Acid (E) | D | D | D |
| Histidine (H) | R, K | R, K | R, K |
| Lysine (K) | R, H | R, H | R, H |
| Arginine (R) | K, H | K, H | K, H |

Conservative amino acid substitutions in the context of a subject peptide are selected so as to preserve activity of the peptide. In one embodiment, a variant polypeptide binds to two or more targets (e.g., proinflammatory targets). More preferably, a variant polypeptide binds to three, four, five, or more pro-inflammatory targets. For example, a variant polypeptide can bind to any combination of targets (e.g., an NF-kB Class II protein and human serum albumin (HSA)). Such binding can be based on in silico, in vitro, or in vivo data.

Modified Polypeptides

Also contemplated in the context of the inventive methods and compositions is the modification of any anti-inflammatory polypeptides described herein, by chemical or genetic means. Examples of such modification include construction of peptides of partial or complete sequence with non-natural amino acids and/or natural amino acids in L or D forms. For example, any of the peptides disclosed herein and any variants thereof could be produced in an all-D form. Furthermore, the polypeptides can be modified to contain carbohydrate or lipid moieties, such as sugars or fatty acids, covalently linked to the side chains or the N- or C-termini of the amino acids. In addition, the polypeptides can be modified to enhance solubility and/or half-life upon being administered. For example, polyethylene glycol (PEG) and related polymers have been used to enhance solubility and the half-life of protein therapeutics in the blood. Accordingly, the polypeptides can be modified by PEG polymers and the like. The polypeptides can also be modified to contain sulfur, phosphorous, halogens, metals, etc. And amino acid mimics can be used to produce polypeptides. In one embodiment, the polypeptides include amino acid mimics have enhanced properties, such as resistance to degradation. For example, the polypeptides can include one or more (e.g., all) peptide monomers.

Treatment/Therapy

In certain embodiments, the present invention provides methods and compositions to treat (e.g., alleviate, ameliorate, relieve, stabilize, delay onset of, inhibit progression of, reduce severity of, and/or reduce incidence of) and/or prevent pancreatic cancer or one or more symptoms associated with pancreatic cancer in a subject. The subject may be human.

The inventive treatment methods comprise administering to a subject a pharmaceutical composition comprising peptide A or peptide B. In certain embodiments, the treatment methods further comprise reducing the expression level and/or activity (by at least 10% (e.g., 15%, 20%, 25%, 30%, 35%, 40%, 45%, 50%, or more)) of at least one pro-inflammatory cytokine(s) at a site of inflammation in a subject. The at least one pro-inflammatory cytokine can be selected from the group consisting of TNFα, IL-1a, IL-6, and IL-12. In other embodiments, the treatment methods inhibit or limit an increase in the expression level and/or activity of at least one of these pro-inflammatory cytokine(s) at a potential site of inflammation in a subject.

Combination Therapy

Additionally, disclosed herein are methods of treatment (and compositions) in which the anti-inflammatory polypeptides (or pharmaceutical compositions comprising such polypeptides) can be administered in combination with at least one other drug or therapy currently known or later discovered to be effective in the treatment of pancreatic cancer. In one embodiment, the drug is a chemotherapeutic agent. In another embodiment, the chemotherapeutic drug is selected from the group consisting of alkylating agents, antimetabolites/nucleoside analogs (for example, 5-fluorouracil, 6-mercaptopurine, capecitabine, cytarabine, floxuridine, fludarabine, gemcitabine, hydroxyurea, methotrexate, pemetrexed, and the like), anti-tumor antibiotics and peptide antibiotics, including anthracyclines (for example, daunorubicin, doxorubicin, epirubicin, idarucicin, and the like), actinimycin-D, bleomycin, mitomycin-C, mitoxantrone, and the like, topoisomerase inhibitors (for example, etoposide, teniposide, mitoxantrone, and the like), mitotic inhibitors (for example, taxanes, epothilones, vinca alkyloids, estramustine, and the like), corticosteroids (for example, prednisone, methylprednisone, dexamethasone, and the like), cytoskeletal disruptors/taxanes, epothilones, histone deacetylase inhibitors, kinase inhibitors, platinum-based agents, retinoids, vinca alkaloids (and derivatives), and other agents including enzymes (for example, L-asparaginase), proteasome inhibitors (for example, bortezomib), therapeutic cancer vaccines, monoclonal antibodies (including tumor-specific monoclonal antibodies), cytokines (for example, IL-2 and IFN-α), and immune checkpoint inhibitors like anti-CTLA4 or anti-PD-1 and anti-PD-1L agents.

The immune system depends on multiple checkpoints to avoid over-activation of the immune system on healthy cells, and tumor cells often take advantage of these checkpoints in order to escape detection by the immune system. CTLA-4, shown to be aberrantly upregulated and present on the surface of T cells in certain cancers, and PD-1, also upregulated in certain tumors and found to inhibit T-cell function, are checkpoints that have been studied as targets for cancer therapy and may be found to be effective in pancreatic cancer (Pardoll, D. M. 2012 Nat Rev Cancer 12(4):252-264; Sharma, et al. 2011 Nat Rev Cancer 11(11):805-812).

Contemplated therapies include surgery (if the pancreatic cancer is confined to the pancreas; if located in the head of the pancreas, a Whipple procedure (pancreatoduodenectomy); if in the pancreatic tail and body, surgery to remove the tail of the pancreas or the tail and a small portion of the body (distal pancreatectomy)); radiation therapy (uses high-energy beams, such as X-rays, to destroy cancer cells); chemotherapy (injected into a vein or taken orally; can be one chemotherapy drug or a combination of chemotherapy drugs); chemotherapy combined with radiation therapy (chemoradiation); targeted therapy (uses drugs that attack specific abnormalities within cancer cells; for example, erlotinib blocks chemicals that signal cancer cells to grow and divide); antibody therapy; gene therapy.

The anti-inflammatory polypeptide(s) can be administered prior to, concurrently with, or after the administration of the additional drug and/or therapy. In one embodiment, the inventive method includes a step of assessing the efficacy of the therapeutic treatment. Such assessment of efficacy can be based on any number of assessment results, including, without limitation, a reduction in tissue inflammation, a suppression or reduction of the excessive production of inflammatory mediators such as IL-1, IL-6, IL-12, and TNF in tissue and/or serum (data not shown), a reduction in the level of inflammatory cytokines (e.g., in the serum), and the like. Depending on the level of efficacy assessed, the dosage of anti-inflammatory polypeptide(s) can be adjusted up or down, as needed.

Thus, by "in combination with," it is not intended to imply that the peptide and additional agent or therapy must be administered at the same time or formulated for delivery together, although these methods of delivery are within the scope of the invention. Furthermore, it will be appreciated that therapeutically active agents utilized in combination may be administered together in a single composition or administered separately in different compositions. In general, each agent will be administered at a dose and/or on a time schedule determined for that agent.

In general, each agent (in this context, one of the "agents" is a composition of this disclosure) will be administered at a dose and on a time schedule determined for that agent. Additionally, the invention encompasses the delivery of the compositions in combination with agents that may improve their bioavailability, reduce or modify their metabolism, inhibit their excretion, or modify their distribution within the body.

The particular combination of therapies (e.g., therapeutics or procedures) to employ in a combination regimen will take into account compatibility of the desired therapeutics and/or procedures and the desired therapeutic effect to be achieved. In general, it is expected that agents utilized in combination will be utilized at levels that do not exceed the levels at which they are utilized individually. In some embodiments, the levels utilized in combination will be lower than those utilized individually.

Diagnosis

In one embodiment, the inventive treatment method additionally comprises diagnosing a subject with pancreatic cancer or, during treatment, diagnosing the efficacy of the treatment method. Pancreatic cancer may be diagnosed by: i) imaging tests (to visualize internal organs, including the pancreas; for example, ultrasound, computerized tomography (CT) scan, and magnetic resonance imaging (MRI)); ii) ultrasound images of the pancreas using an endoscopic ultrasound (EUS) from inside the abdomen; iii) blood test (to test for specific proteins (including tumor markers) shed by the pancreatic cancer cells); iv) laparoscopy (surgical visualization of the pancreas); iv) endoscopic retrograde cholangiopancreatography (ERCP); v) biopsy (for example, via fine-needle aspiration or during ERCP) to remove a small sample of tissue from the pancreas for examination under a microscope; and/or vi) percutaneous transhepatic cholangiography (PTC).

Compositions for Treating Pancreatic Cancer and Administration

Compositions for treating pancreatic cancer of this disclosure may be formulated according to any of the conventional methods known in the art and widely described in the literature. Thus, the active ingredient (e.g., peptide A or peptide B, or variants thereof) may be incorporated, optionally together with other active substances, with one or more conventional pharmaceutically acceptable carriers, diluents and/or excipients, etc., appropriate for the particular use of the composition, to produce conventional preparations that are suitable or can be made suitable for administration. They may be formulated as liquids, as semi-solids or solids, liquid solutions, dispersions, suspensions, and the like, depending on the intended mode of administration and therapeutic application. In some embodiments, the inventive composition is prepared in a form of an injectable or infusible solution.

Compositions for treating pancreatic cancer of this disclosure may include a carrier protein, such as serum albumin (e.g., HSA, BSA, and the like). The serum albumin can be purified or recombinantly produced. By mixing the anti-inflammatory polypeptide(s) in the pharmaceutical composition with serum album, the anti-inflammatory polypeptides can be effectively "loaded" onto the serum albumin, allowing a greater amount of anti-inflammatory polypeptide to be successfully delivered to a site of inflammation.

Methods of treating pancreatic cancer of this disclosure may include administration via any one of a variety of routes, including intravenous (IV), intramuscular (IM), intra-arterial, intramedullary, intrathecal, subcutaneous (SQ), intraventricular, transdermal, interdermal, intradermal, by intratracheal instillation, bronchial instillation, and/or inhalation; as a nasal spray, and/or aerosol, and/or through a portal vein catheter. In certain embodiments, intravenous injection, or infusion may be used. Any appropriate site of administration may be used. For example, the inventive composition may be administered locally and directly at the site where action is required or may be attached or otherwise associated, e.g. conjugated, with entities which will facilitate the targeting to an appropriate location in the body.

In these compositions useful in the treatment of pancreatic cancer, any physiologically compatible carrier, excipient, diluent, buffer or stabilizer may be used. Examples of suitable carriers, excipients, diluents, buffers and stabilizers include one or more of water, saline, phosphate buffered saline, dextrose, glycerol, ethanol and the like, as well as combinations thereof. In some cases isotonic agents, e.g., sugars, polyalcohols (e.g., mannitol, sorbitol), or sodium chloride may be included. In certain embodiments, the compositions of the invention may be formulated so as to provide quick, sustained, or delayed release of the active ingredient (peptide A, peptide B, or variants thereof and/or additional drug(s)) after administration to the subject by employing procedures well known in the art. As described above, in certain embodiments, the composition is in a form suitable for injection and suitable carriers may be present at any appropriate concentration, but exemplary concentrations are from 1% to 20% or from 5% to 10%.

Therapeutic compositions typically must be sterile and stable under conditions of manufacture and storage. Appropriate ways of achieving such sterility and stability are well known and described in the art.

Pharmaceutical compositions are typically formulated in unit dosage form for ease of administration and uniformity of dosage. It will be understood, however, that the total daily (or other) usage of the compositions of the present invention will be decided by the attending physician within the scope of sound medical judgment. The specific therapeutically effective dosage level for any particular subject will depend upon a variety of factors including the activity of the composition employed; the half-life of the composition after administration; the age, body weight, general health, sex, and diet of the subject; the time of administration, route of administration, and rate of excretion of peptide A and (if used) the additional therapeutic agent employed; the duration of the treatment; drugs used in combination or coincidental with the specific compound employed; and like factors, well known in the medical arts. Furthermore, effective doses may be extrapolated from dose-response curves derived from in vitro and/or in vivo animal models.

Thus, suitable doses of the peptide of this disclosure and other active ingredients (if included) will vary from patient to patient and will also depend on the stage of the pancreatic cancer. In some embodiments, said dosages constitute a therapeutically effective amount or a prophylactically effective amount, depending on the nature of the treatment involved. The ability of the peptide to elicit a desired response in the individual will also be a factor. Exemplary daily doses are: 0.1 to 250 mg/kg, or 0.1 to 200 or 100 mg/kg, or 0.5 to 100 mg/kg, or 1 to 50 or 1 to 10 mg/kg, of the active ingredient. This can be administered as a single unit dose or as multiple unit doses administered more than once a day, for example, subcutaneously, intraperitoneally, or intravenously. It is to be noted, however, that appropriate dosages may vary depending on the patient, and that for any particular subject, specific dosage regimes should be adjusted over time according to the individual needs of the patient. Thus, the dosage ranges set forth herein are to be regarded as exemplary and are not intended to limit the scope or practice of the claimed compositions or methods.

Kits for Treating Pancreatic Cancer

In one aspect, the invention further provides kits for the treatment of pancreatic cancer comprising peptide A and/or peptide B, or variants thereof, or a composition comprising the same. Kits can include one or more other elements including, but not limited to, instructions for use; other therapeutic agents (i.e., for combination therapy of pancreatic cancer); other reagents, e.g., a diluent, devices or other materials for preparing composition for administration; pharmaceutically acceptable carriers; and devices or other materials for administration to a subject. Instructions for use can include instructions for therapeutic application, including suggested dosages and/or modes of administration, e.g., in a human subject, as described herein. In some embodiments, said kits are for use in the methods and uses as described herein, e.g. therapeutic, diagnostic, or imaging methods, or are for use in in vitro assays or methods.

In some embodiments, said kits are for diagnosing pancreatic cancer and optionally comprise instructions for use of the kit components to diagnose pancreatic cancer.

Animal Models

As noted above, one major hurdle in improving prognosis for subjects with pancreatic cancer is the lack of a therapeutic time window. Early cancerous lesions are far beneath the threshold of detection. By the time of diagnosis, even early (T1) tumors can be metastatic and resistant to conventional treatments. A discrepancy between experimental success in vitro and in vivo and disappointment in clinical trials likely results from the inefficiency of current experimental setups in recreating the tumor microenvironment. The fibrotic stroma of pancreatic ductal adenocarcinoma, which can form more than 80% of the tumor mass, are not a passive scaffold for the malignant cells; rather, they play an active role in carcinogenesis. This is a component is frequently missing in the xeno-/allograft-mouse models (Erkan, et al. 2012 *Curr Mol Med* 12(3):288-303; Olive, et al. 2009 *Science* 324(5933):1457-61).

Thus, models of pancreatic cancer in animals are critical to the pre-clinical testing of Peptide A. The KP16 transgenic mouse model, considered the gold standard for drug development in pancreas cancer, is a Ras-driven conditional pancreas cancer model (knock-in of the pancreas cancer-specific Ras G12D allele and knock-out of the p16/p19 locus) (Aguirre, et al. 2003 *Genes & Dev* 17(24):3112-26). These animals develop spontaneous pancreas cancer that is very much like human pancreatic cancer. In addition, the animals are fully immune competent. While the homozygous mouse has an average lifespan, the knockout mouse has a lifespan of about 59 days.

The heterotopic HPAC xenograft model constitutes human HPAC cancer cells implanted into immunocompromised mice. The heterotopic HPAC xenograft model has previously been successfully used to evaluate the merit of immunotherapy in pancreatic cancer (Abate-Daga, et al. 2014 *Hu Gene Ther* 25(12):1003-1012).

EXAMPLES

The following examples are provided for illustrative purposes only and are not intended to limit the scope of the invention.

Example 1. Polypeptide Binding

Peptide A was identified as having anti-inflammatory activity via peptide binding studies targeting specific components of various signaling pathways that regulate inflammation. Peptide binding was previously evaluated using the web-based ClusPro™ algorithm developed at Boston University. Peptide A demonstrated high binding affinity for RelB, TGFβ, Notch1, Wnt8R, TRAIL, IL-6R, IL-10R, EGFR, and CDK6. Peptide A also demonstrated high binding affinity for histone modification enzyme HMT, as well as proteins relevant to macrophage activity and apoptosis (both associated with inflammation and tumor genesis and metastasis), such as CD47, SIRP-α, CD206, and TGM2. Finally, peptide A was found to have high binding affinity for human serum albumin (HSA). Serum albumin is the most abundant protein in the circulation, and solid tumors, particularly pancreatic tumors, will take up serum albumin into their cells (through the process of pinocytosis) and use it as an energy source.

Given the significant role of inflammation in tumor genesis and metastasis, the known association of M2 macrophage activity with tumor development, and the indications that the CD47/SIRP interaction is capable of disabling the activity of M1 macrophages, it was anticipated that the administration of peptides of this disclosure could positively influence the outcomes of pancreatic cancer treatment.

Example 2. Peptide A Suppresses In Vivo Tumor Growth in KP16 Mouse Model

Peptide A improved survival in combination with gemcitabine in the KP16 transgenic mouse model of pancreatic cancer (FIG. 1B). Mice with the desired genotype (Pdx-1-Cre; LSL-KrasG12D/+; Ink4a(p16)/Arf(p19)flox/flox) were selected and screened with transabdominal ultrasound starting week 6. Tumors between 2-4 mm$^2$ were selected for treatment. Mice with tumors were randomly assigned to the following treatments: vehicle (intraperitoneal injection of 100 μl H$_2$O or PBS); 50 mg/kg twice weekly gemcitabine by intraperitoneal injection in a volume of 100 μl PBS; 20 mg/kg Peptide A twice weekly given by intraperitoneal injection in 100 μl H$_2$O; and the combination of Peptide A given at a dose of 20 mg/kg twice weekly with 50 mg/kg gemcitabine twice weekly in their respective dissolvents. Peptide A halted growth of pancreatic cancers in the transgenic animals (FIGS. 1A and 1B; Peptide A is shown as 'RP-182').

Peptide B, equally demonstrated anti-tumor activity in combination with gemcitabine, both extension of survival and reduction of tumor growth.

Figure 2:
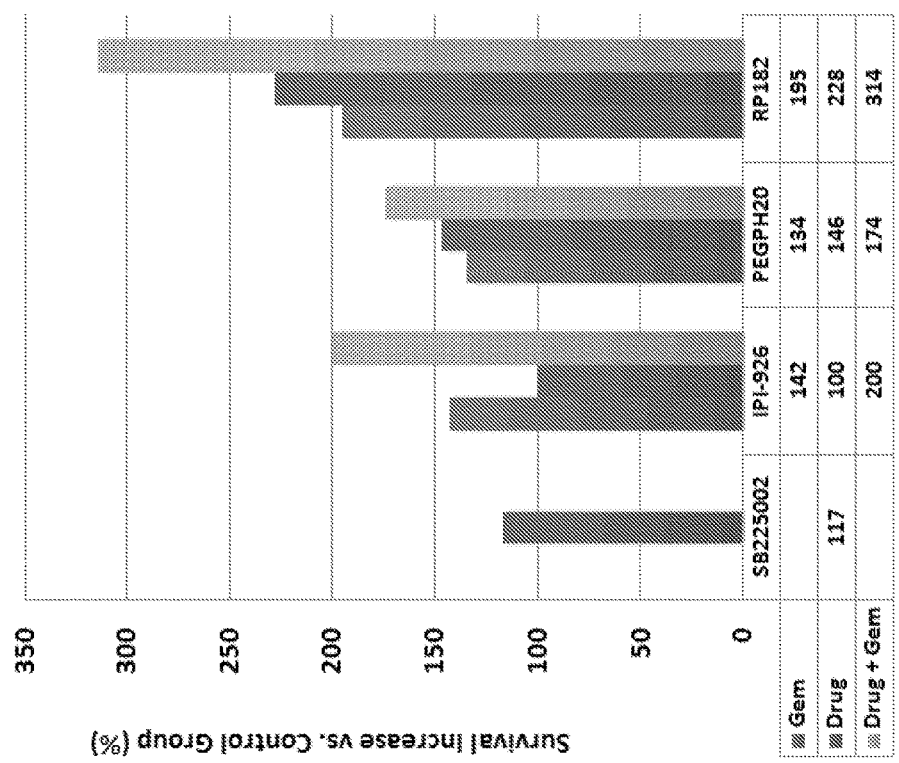
FIG. 2 shows a comparison of Peptide A administration (alone and in combination with gemcitabine) to other investigational agents (also tested alone and in combination with gemcitabine) in transgenic animal models of pancreatic cancer.

Example 3. Peptide A+Bemcitabine Demonstrates Greater Efficacy Than Other Agents in Pancreatic Cancer When the combination of peptide A and gemcitabine (peptide A+gemcitabine) was compared to other investigational agents that are in clinical trials (one even having obtained regulatory approval), each in a comparable animal model of pancreatic cancer, Peptide A showed a greater percentage increase in average survival over controls. The investigational drugs used for comparison purposes include SB225002/TgfbrKO/Kras, which inhibits CXCR2 and disrupts tumor-stromal interactions and improves survival in a mouse model of pancreatic ductal adenocarcinoma (see, Hideaki Ijichi, et al. 2011; The Journal of Clinical Investigation; in this paper, only data for the drug and vehicle control are provided); IPI-926/Trp53R172H/Kras which inhibits Hedgehog signaling and enhances delivery of chemotherapy in a mouse model of pancreatic cancer (see, Kenneth P. Olive et al. 2009; Science); PEGH20/Trp53R172H/Kras, with enzymatic targeting of the stroma and ablates physical barriers to treatment of pancreatic ductal adenocarcinoma (see, Paolo Provenzano et al. 2012; Cancer Cell). For each of the cited studies, overall survival outcomes were reviewed and outcome of the vehicle-treated cohort was set as control. Change in survival or change in tumor growth (as recorded median in the original publications) was graphed as change of % per cohort (FIG. 2; peptide A is shown as 'RP182').

The other investigational agents used for comparative testing included SB225002 tested in the Ras-driven Tgf-br$^{KO}$/KrasG12D animal model (Ijichi, et al. 2011 *J Clin Invest*), or IPI-926 tested in the Pdx/Trp53R172H/KrasG12D KPC model (Olive, et al. 2009 *Science*), or PEGH20 also tested in the Pdx/Trp53R172H/KrasG12D KPC model (Provenanzo, et al. 2012 *Cell*), with IPI-926 and PEGH20 given both as single agents or in combination with gemcitabine.

Figure 3:
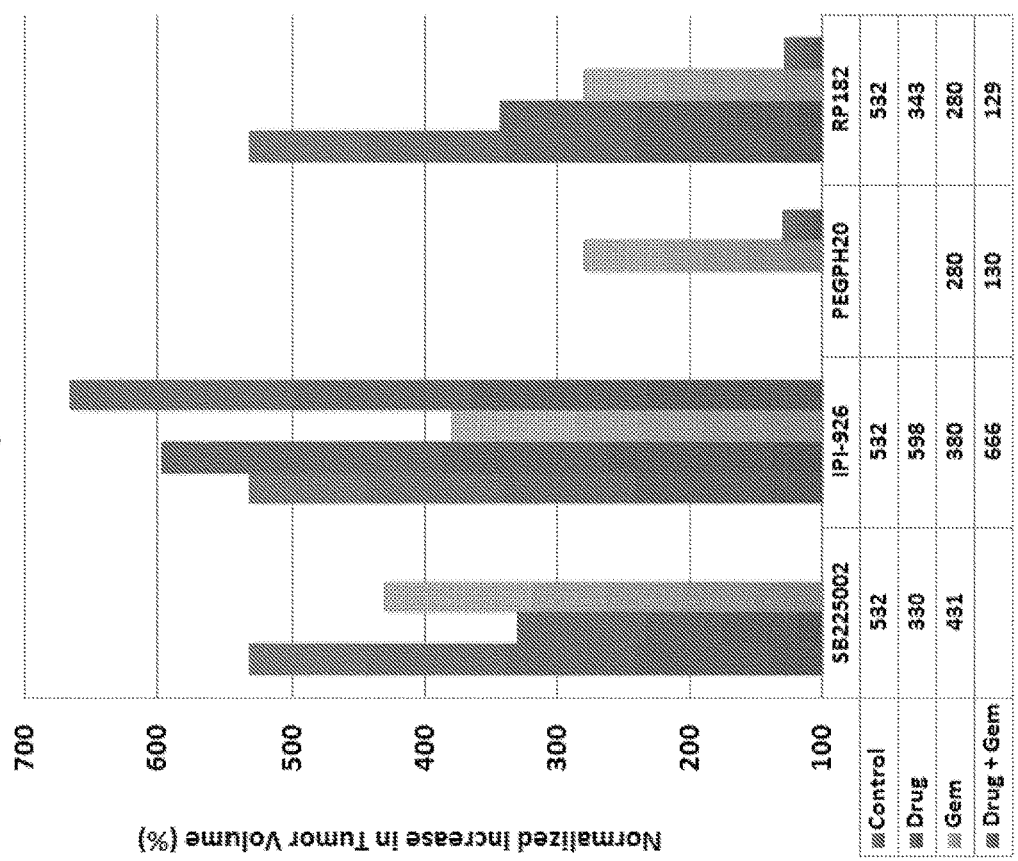
FIG. 3 shows a comparison of percent change in normalized average tumor volumes for pancreatic tumors following administration of peptide A (shown as 'RP182') and other known investigational anti-cancer agents.

Peptide A+gemcitabine also exhibited a strong (and comparable, if not slightly improved) reduction in tumor growth, as shown in terms of percent change in normalized average tumor volumes (FIG. 3; peptide A is shown as 'RP182'). The other investigational agents used for comparative testing included SB225002; IPI-926 (investigational treatment for pancreatic adenocarcinoma from Infinity Pharmaceuticals); PEGH20 (recommended for combined treatment with nab-paclitaxel (ABRAXANE®) and gemcitabine; received regulatory approval in 2014; note that in the PEGPH20 paper there are tumor volume data for only the Gemcitabine and Drug+Gemcitabine treatments).

Figure 4:
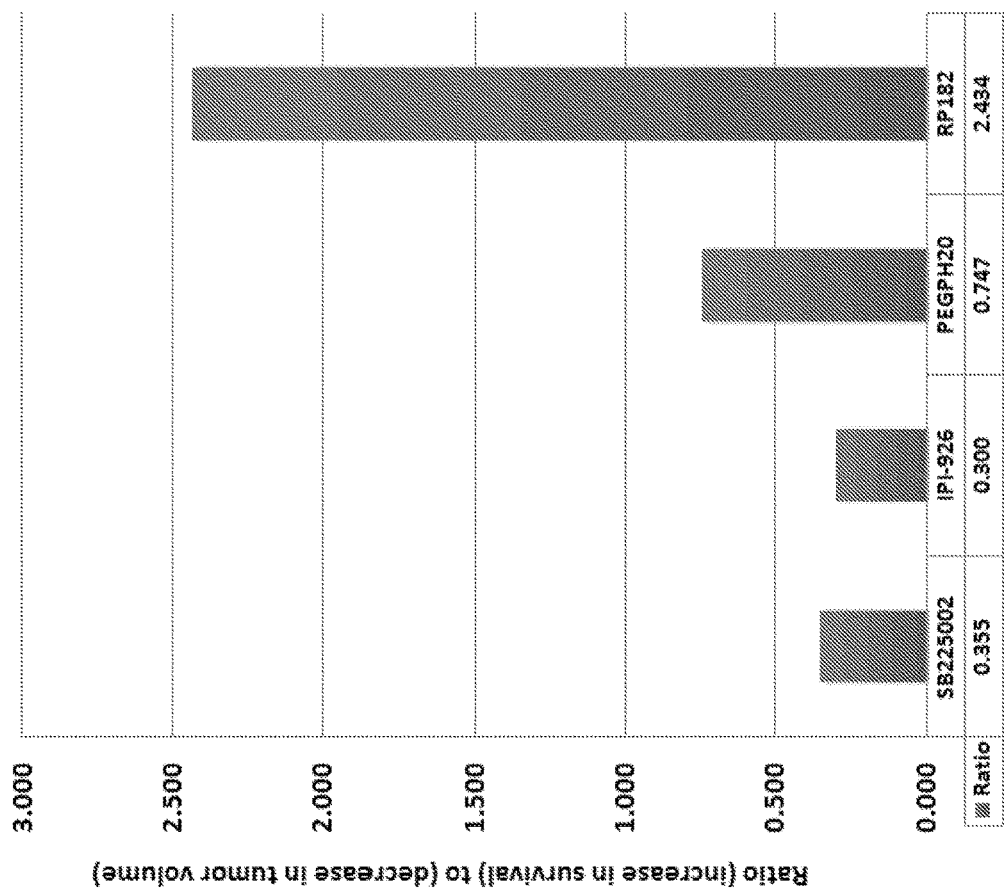
FIG. 4 shows a summary of the relative benefit of Peptide A (peptide A is shown as 'RP182') and other investigational agents used in combination with gemcitabine in transgenic animal models of pancreatic cancer as a ratio of the percent increase in survival over percent change in tumor volume.

The relative benefit of the investigational agents in combination with gemcitabine in transgenic animal models of pancreatic cancer as a ratio of % increase in survival over % change in tumor volume is summarized in FIG. 4 (peptide A is shown as 'RP182'). Compared to the afore-mentioned investigational agents subsequently moved into clinical trials, the combination of Peptide A with gemcitabine showed the greatest reduction of tumor growth associated with the most extension of survival.

Example 4. Peptide A Shows Specific Cellular Binding

Figure 5:
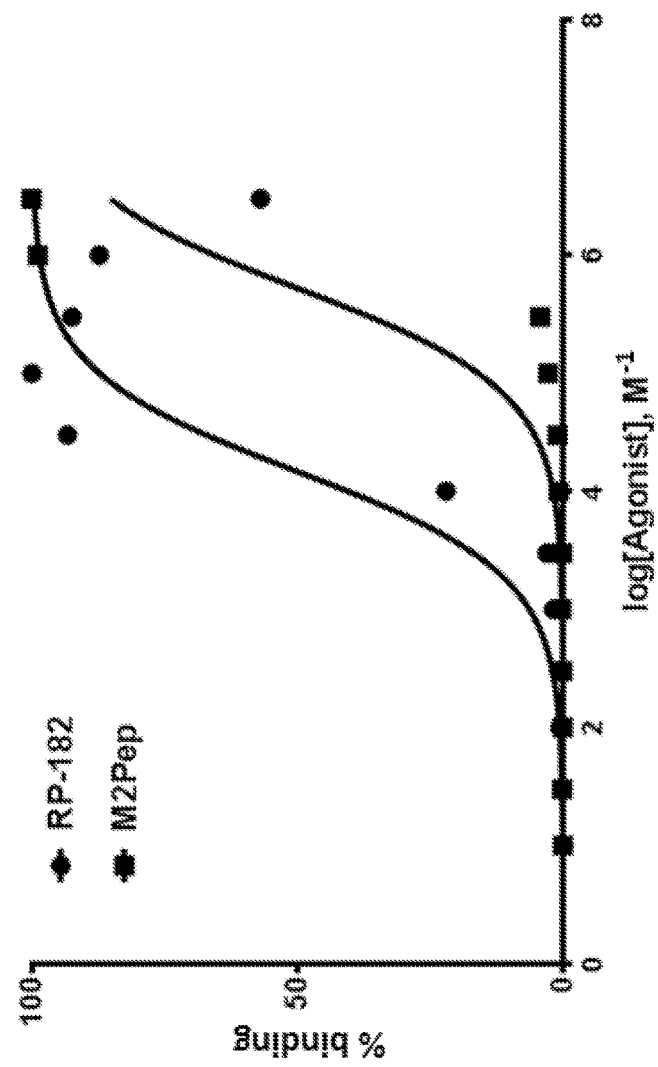
FIG. 5 shows a comparison of binding of a C-terminus-biotinylated Peptide A with a random 10 mer-biotinylated peptide demonstrating that Peptide A binding is specific to p16 pancreatic cancer cells.

In order to elucidate the cellular and/or molecular targets of Peptide A, the latter's binding to p16 pancreatic cancer cells was compared to the binding of a random 10 mer peptide. C-terminus biotin-labelled (via 8(gly) linker+cys) was incubated at increasing concentrations for 10 minutes with p16 pancreatic cancer cells, excess peptide was washed off, and cells were re-incubated with fluoro-labelled streptavidin and analyzed by flow cytometry. The fraction of streptavidin-labelled cells to total cells was graphed for each concentration, and full EC50 drug-binding curves were constructed (Inglese, et al. 2006 *PNAS USA* 103(31):11473-8). As shown in FIG. 5, comparison of the binding of the C-terminus-biotinylated Peptide A (RP-182') with a random 10 mer biotinylated peptide ('Elim peptide') showed that Peptide A binding is specific to p16 pancreatic cancer cells. The shape and configuration of the binding curve (full class Ia curve, sigmoidal shape) compared to the no (or unspecific) binding of the control 10-mer peptide indicates 'facilitated binding,' i.e., binding through a specific cell surface mechanism, which is in agreement with in silico computer modeling data. Additionally, Peptide A exhibited more than five-fold stronger binding to the cancer cells than the control 10 mer peptide (FIG. 5).

Example 5. Peptide A Binds to Cells Via its N-Terminus

Figure 6:
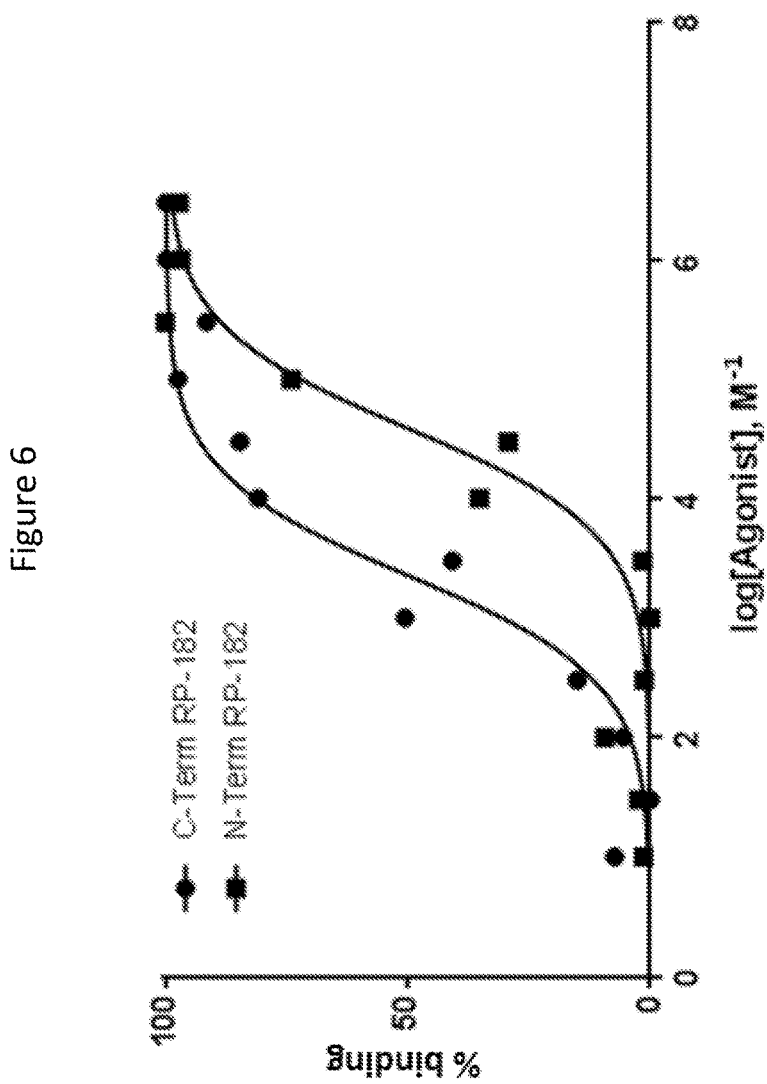
FIG. 6 shows the cellular binding curve for N- and C-terminally labelled Peptide A binding indicating preferred binding of Peptide A to cancer cells via the N-terminus.

In order to determine whether Peptide A binds to cancer cells via its N- or C-terminus, the cellular binding of N- and C-terminally labelled Peptide A (RP-182'), followed by determination of bound: unbound cell fraction via flow cytometry, was carried out as in the previous example. The EC50 curve in FIG. 6 shows the preferred binding of cancer cells via the N-terminus. Steric hindrance through biotinylation of the N-terminus of Peptide A leads to a log-fold decreased cellular binding.

Example 6. Peptide A Suppresses In Vivo Tumor Growth in a Xenograft Model of Pancreatic Cancer Peptide A was tested in another mouse model of pancreatic cancer: the heterotopic HPAC xenograft model (human HPAC cancer cells implanted into immunocompromised mice). $1 \times 10^6$ human pancreas cells, luciferase-tagged, were injected into 32 nude athymic mice. The mice were then given (injected with) vehicle, Peptide A, gemcitabine, or Peptide A+gemcitabine at concentrations of 20 mg/kg intraperitoneally twice weekly for Peptide A and 120 mg/kg gemcitabine once weekly. After 4 weeks of treatment, tumor and spleen were harvested, and CD11b+magnetic cell separation was carried out. Isolated CD11b+cells were cocultured with HPAC in vitro. Cancer cell viability was quantified via luciferase activity of luciferase-tagged cancer cells. CD11b-positive cells obtained from Peptide A-treated animals inhibited cancer cell growth compared to CD11b-cocultured cells obtained from vehicle-treated animals.

Figure 7:
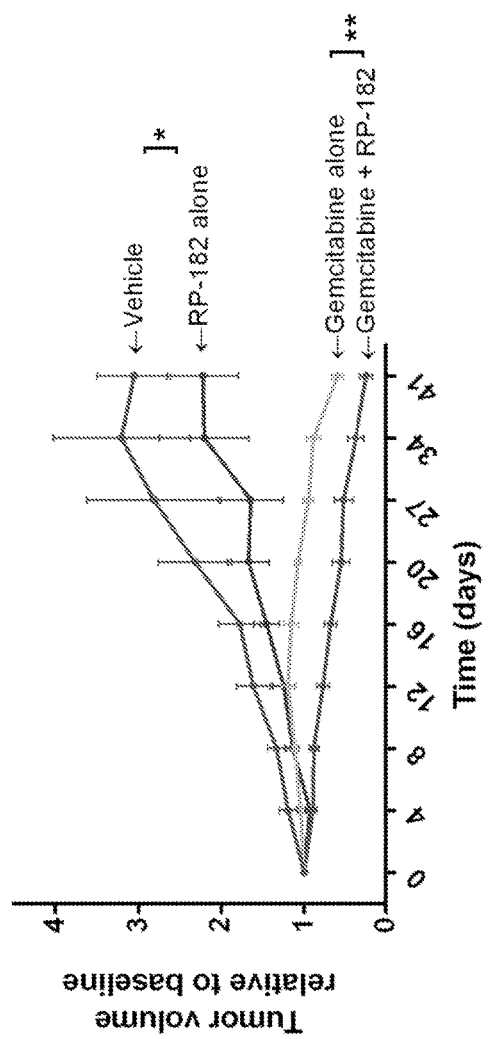
FIG. 7 shows a comparison of different drug treatments in a xenograft model of pancreatic cancer. For vehicle vs. RP-182 alone (*), p=0.007. For gemcitabine alone vs. Gemcitabine +RP-182 (**), p<0.007.

Peptide A was found to suppress in vivo tumor growth in a xenograft model of pancreatic cancer. As shown in FIG. 7, HPAC pancreatic cancer cell xenografts were treated with vehicle, Peptide A (indicated as 'RP-182' in FIG. 7), Gemcitabine and the combination of Gemcitabine and Peptide A ("Gemcitabine+RP-182"), until mice reached their pre-determined endpoint (euthanasia directed by the study veterinarian) and tumors were weighed. Tumor volume was recorded as a change to vehicle-treated mice. Peptide A did not demonstrate toxicity in the xenograft mouse model of pancreatic cancer (data not shown). Statistically significant differences in tumor volume between vehicle and Peptide A (*$p=0.007$) and gemcitabine alone and gemcitabine combined with Peptide A (**$p<0.001$) were seen.

Example 7. Peptide B Affects the Immune System in Pancreatic Cancer

Figure 8:
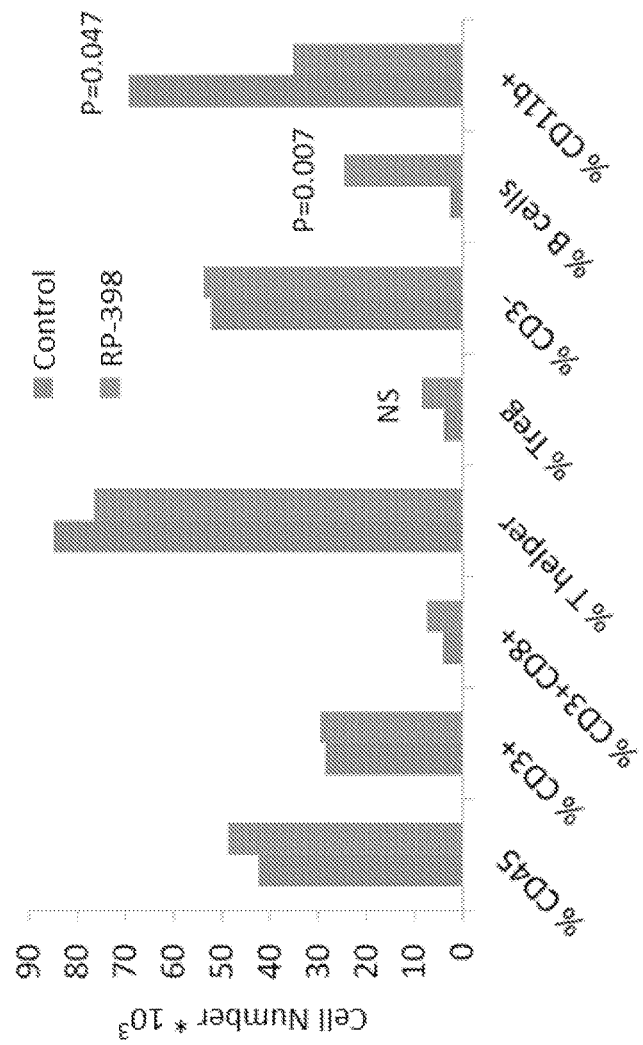
FIG. 8 shows an analysis of immune system cells in pancreatic cancer following treatment with Peptide B, indicating that Peptide B treatment increases B cells, and reduces macrophages in these pancreatic tumors.

In an effort to investigate whether or not Peptide B affects the immune system in pancreatic cancers, P16 tumors treated with vehicle vs. 2 mg/kg daily intraperitoneally with peptide B were excised, digested, incubated with previously titrated and optimized immune cell markers, and analyzed by multi-color flow cytometry. Cell fractions of various cell subpopulations are shown in FIG. 8. Peptide B (shown as 'RP-398') was found to affect the immune system in pancreatic cancer by increasing B cells in these tumors, and reducing macrophages in these tumors.

Example 8. Tumor-Associated Macrophages Behave Differently Coming from Untreated vs. Treated Mice Macrophages isolated from Peptide A-treated vs. untreated tumors were found to behave differently. Treated HPAC xenotransplants, either with vehicle or 20 mg/kg Peptide A by intraperitoneal injection twice weekly were harvested when >1.5 cm, digested, and CD11b cells isolated by magnetic bead pull-down. Enrichment of CD11b-positive cells following pull-down >80% was confirmed by flow cytometry. Isolated CD11b-positive cells were co-cultured with 5,000 luciferase-tagged HPAC cells at ratios 3:1 and 10:1, and growth of cancer cells was determined using luciferase-tag activity. Macrophages from Peptide A-treated tumors had increased anti-tumor activity and stopped the growth of cancer cells when co-cultured with them (data not shown).

Example 9. Peptide A can be Measured in Murine and Human Sera

Mass spectrometry was used to quantify Peptide A in the serum of mouse (data not shown). Intraperitoneal injection at the dose used in the mouse studies described herein led to a measurable serum concentration that can exert a biological effect. Peptide A was detectable at an ion mass spectrometer with a mass of 688.08 after 5 minutes with a prolonged gradient. Spike-in experiments of peptide A into mouse serum confirmed identical mass and time-of-flight. Calculated serum concentrations (ng/ml) were in line for peptide A to be able to exert biological function (data not shown). This ability to measure the peptide in mouse serum is the basis for pharmacokinetic and toxicity studies.

The invention claimed is:

1. A method for treating pancreatic cancer in a subject comprising administering to the subject in need thereof a peptide comprising the amino acid sequence Lys-Phe-Arg-Lys-Ala-Phe-Lys-Arg-Phe-Phe (SEQ ID NO:1) or a multimer, derivative, or variant thereof.

2. The method of claim 1, wherein the peptide is conjugated to a polyethylene glycol linker.

3. The method of claim 1, wherein the peptide is administered as at least one of a dimer or a tetramer of SEQ ID NO:1, or a combination thereof.

4. The method of claim 1, wherein the administering further comprises the administration of an additional therapeutic agent.

5. The method of claim 4, wherein the therapeutic agent is a chemotherapeutic agent.

6. The method of claim 5, wherein the chemotherapeutic agent is selected from the group consisting of gemcitabine and an immune checkpoint inhibitor.

7. The method of claim 5, wherein the chemotherapeutic agent is gemcitabine, Abraxane, or FOLFIRINOX (fluorouracil, leucovorin, irinotecan, oxaliplatin regimen).

8. The method of claim 1, wherein the administration is parenteral.

9. The method of claim 1, wherein the peptide is administered at a dosage of 0.05 to 25 mg/kg.

10. The method of claim 1, wherein the subject is human.

11. The method of claim 1, wherein the peptide comprises the amino acid sequence Lys-Phe-Arg-Lys-Ala-Phe-Lys-Arg-Phe-Phe (SEQ ID NO:1) or a multimer thereof.

12. The method of claim 11, wherein the peptide is a monomer.

13. The method of claim 1, wherein the peptide comprises the amino acid sequence Lys-Phe-Arg-Lys-Ala-Phe-Lys-Arg-Phe-Phe (SEQ ID NO:1) or a variant thereof having one substitution in one amino acid residue at one position of the sequence.

14. The method of claim 13, wherein the peptide consists of the amino acid sequence Lys-Phe-Arg-Lys-Ala-Phe-Lys-Arg-Phe-Phe (SEQ ID NO:1).

15. The method of claim 14, wherein the administering further comprises the administration of a chemotherapeutic agent.

16. The method of claim 15, wherein the chemotherapeutic agent is selected from the group consisting of gemcitabine and an immune checkpoint inhibitor.

17. The method of claim 15, wherein the chemotherapeutic agent is gemcitabine, Abraxane, or FOLFIRINOX (fluorouracil, leucovorin, irinotecan, oxaliplatin regimen).

\* \* \* \* \*

UNITED STATES PATENT AND TRADEMARK OFFICE
CERTIFICATE OF CORRECTION

PATENT NO. : 10,016,480 B2
APPLICATION NO. : 15/518216
DATED : July 10, 2018
INVENTOR(S) : Udo Rudloff et al.

It is certified that error appears in the above-identified patent and that said Letters Patent is hereby corrected as shown below:

In the Specification

At Column 13, Line 1, replace "Bemcitabine" with --gemcitabine--

Signed and Sealed this
Eighth Day of January, 2019

Andrei Iancu
*Director of the United States Patent and Trademark Office*